United States Patent
Wagner

(10) Patent No.: US 7,604,875 B2
(45) Date of Patent: Oct. 20, 2009

(54) MITIGATION OF ARTIFACTS IN NUCLEAR MAGNETIC RESONANCE IMAGING WITH MAGNETIC SUSCEPTIBILITY MODIFIED MATERIALS

(75) Inventor: Shawn Wagner, Altadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 11/895,873

(22) Filed: Aug. 28, 2007

(65) Prior Publication Data

US 2008/0063890 A1  Mar. 13, 2008

Related U.S. Application Data

(60) Provisional application No. 60/842,759, filed on Sep. 7, 2006.

(51) Int. Cl.
  *B32B 15/00* (2006.01)
(52) U.S. Cl. .................. 428/692.1; 428/615; 428/457; 428/693.1; 428/704; 252/62.51 R
(58) Field of Classification Search .............. None
  See application file for complete search history.

(56) References Cited

U.S. PATENT DOCUMENTS

2006/0102871 A1* 5/2006 Wang et al. ........... 252/62.51 R

OTHER PUBLICATIONS

CRC Handbook of Chemistry and Physics, David R. Lide, 79th Edition, 1998-1999.*
Paramagnetic Effects of Iron(III) Species on Nuclear Magnetic Relaxation of Fluid Protons in Porous Media Traci R. Bryar, 1 Christopher J. Daughney, and Rosemary J. Knight Department of Earth and Ocean Sciences, University of British Columbia, Vancouver, British Columbia V6T 1Z4, Canada Received Mar. 25, 1999: Revised Jul. 29, 1999.*
Measurement Science Review, vol. 6, Section 2, No. 2, 2006 Evaluation of MRI artifacts caused by metallic dental implants and classification of the dental materials in use 1 Z. Starčuk, 1K. Bartušek, 2H. Hubálková, [4]T. Bachorec, [1]J. Starčuková, [3]P. Krupa.*

* cited by examiner

*Primary Examiner*—D. Lawrence Tarazano
*Assistant Examiner*—Gary D. Harris
(74) *Attorney, Agent, or Firm*—Seth Z. Kalson

(57) ABSTRACT

Materials suitable for medical and dental implants with magnetic susceptibility matched to surrounding environment to reduce artifacts in nuclear magnetic resonance imaging. Paramagnetic and diamagnetic materials may be added to ceramics and polymer resins to adjust magnetic susceptibility. Other embodiments are described and claimed.

2 Claims, 2 Drawing Sheets

MITIGATION OF ARTIFACTS IN NUCLEAR MAGNETIC RESONANCE IMAGING WITH MAGNETIC SUSCEPTIBILITY MODIFIED MATERIALS

BENEFIT OF PROVISIONAL APPLICATION

This application claims the benefit of U.S. Provisional Application No. 60/842,759, filed 7 Sep. 2006.

FIELD

The present invention relates to nuclear magnetic resonance imaging and magnetic materials.

BACKGROUND

Nuclear magnetic resonance (NMR) refers to the response of atomic nuclei to magnetic fields. It is applicable to nuclei having an odd number of protons or neutrons, or both. In many applications, the nuclei is that of hydrogen (a proton), where the hydrogen is part of the water molecule.

A static magnetic field is applied to the sample of interest, which causes a precession of the nuclei at the Larmor frequency, proportional to the strength of the applied static magnetic field. The applied static magnetic field has a non-zero spatial gradient, so that the Larmor frequency of a nucleus is a function of its position in the sample of interest. The macroscopic magnetization is parallel with the direction of the static magnetic field.

Applying an oscillating magnetic field perpendicular to the static magnetic field and at a frequency equal to the Larmor frequency tips the magnetization. The tip angle is proportional to the product of the amplitude of the oscillating magnetic field with the time over which it is applied. The nuclei with the Larmor frequency precess in phase with one another.

A 90° pulse refers to a pulsed oscillating magnetic field that tips the magnetization to a direction along a plane transverse to the direction of the static magnetic field. After the 90° pulse, the nuclei population begins to dephase, that is, they lose their phase coherency. This decreases the net magnetization, which may be detected by a receiver coil. The measured decay is called the free induction decay.

In spin-echo detection, a sequence of 180° pulses (oscillating magnetic field pulses that change the tip angle by 180°) follows the 90° pulse. The first 180° pulse reverses the dephasing of the magnetization among the nuclei population, so that after some period of time the nuclei tend to be in phase, and a spin-echo signal is generated that is detectable in a receiver coil. The sequence of 180° pulses causes a sequence of spin-echo signals, but with decreasing signal strength over the sequence of 180° pulses.

In gradient-echo detection, a sequence of gradient defocusing and focusing follows an excitation pulse. The application of the defocusing and refocusing magnetic gradient changes generates a detectable echo signal in a receiver coil, but with decreasing signal strength with increasing repetitions of magnetic gradient defocusing and refocusing, and increases in time required for magnetic gradient defocusing and refocusing.

Because the Larmor frequency is a function of position due to the gradient in the static magnetic field, NMR imaging is realized by changing the frequency of the oscillating magnetic nuclei and analyzing the resulting spin-echo or gradient-echo signals. However, in applications to medical imaging of the human body, there may be various medical implants whose magnetic susceptibility does not match that of the surrounding tissue. A mismatch in magnetic susceptibility will affect the magnetization, which may lead to imaging artifacts in NMR. For example, relatively small deviations in the magnetic field may result in the displacement of several voxels when performing NMR imaging. Furthermore, signal loss may occur due to dephasing. During the acquisition when the free induction signal is refocused, the average frequency of the protons should remain constant. But in areas where there are deviations in the magnetic field homogeneity, the received signal is reduced because of the loss in refocusing.

Acrylics used in dental work are manufactured to be radio-opaque, so that they may be imaged in an x-ray. However, various materials in the acrylics may have a susceptibility different from that of air or water, which may cause unwanted artifacts in an NMR image. As another example, various ceramics may be used in hip replacements and other medical implants, where the magnetic susceptibilities of such ceramics may not match the surrounding tissue susceptibility (e.g., the susceptibility of water).

DESCRIPTION OF EMBODIMENTS

In the description that follows, the scope of the term "some embodiments" is not to be so limited as to mean more than one embodiment, but rather, the scope may include one embodiment, more than one embodiment, or perhaps all embodiments.

Figure 1:
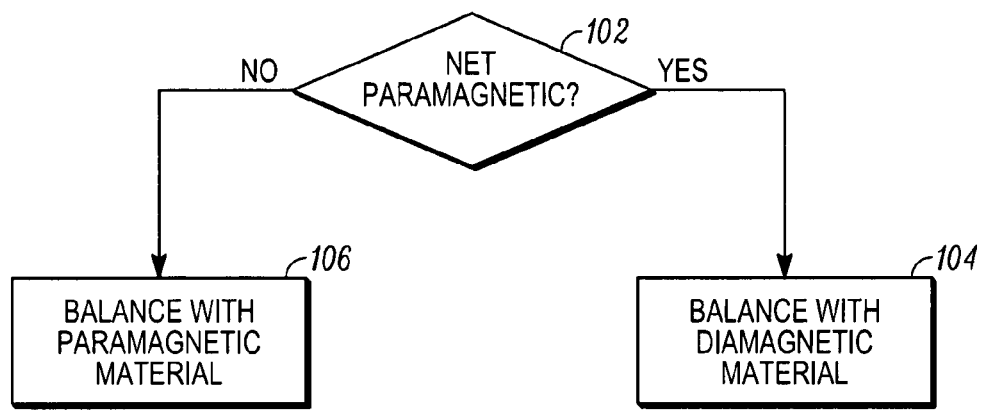
FIG. 1 illustrates a flow diagram according to an embodiment of the present invention.

Embodiments provide for biocompatible materials having a magnetic susceptibility matched to their surrounding tissue, or to air. For isotropic and linear materials, the magnetic induction $\vec{B}$ and the magnetic field $\vec{H}$ are related by $\vec{B} = \mu_0(1+\chi_m)\vec{H}$, where $\mu_0$ is the permeability of free space, and $\chi_m$ is the magnetic susceptibility. The permeability $\mu$ is $\mu=(1+\chi_m)$. Paramagnetic material has a positive magnetic susceptibility, so that the permeability is greater than one. In this case, the magnetic induction is increased in the material when compared to free space. Diamagnetic material has a negative magnetic susceptibility, so that the permeability is less than one. In this case, the magnetic induction is decreased in the material when compared to free space. Embodiments modify NMR imaging compatible materials to make their magnetic susceptibility closer to air, or human tissue, by balancing net paramagnetic material with diamagnetic material, and by balancing net diamagnetic material with paramagnetic material. This procedure is illustrated in the flow diagram of FIG. 1. If a material is measured as paramagnetic (102), then diamagnetic material is added (104) to bring the magnetic susceptibility sufficiently close to the intended surrounding tissue, whereas if the material is diamagnetic, then paramagnetic material is added (106).

Embodiments may use one or more diamagnetic materials selected from the group: $Al_2O_3$; $Al_2(SO_4)_3$; $Al2(SO_4)_3 * 2H_2O$; $Sb_2O_3$; $BaO$; $BaO_2$; $Bi$; $BiI_3$; $BiO$; $Bi_2(SO_4)_3$; $Bi_2S_3$; $B_2O_3$; $Ca(C_2H_3O_2)_2$; $CaBr_2 * nH_2O$; $GaI_3$; $Ga_2O$; $GeO$; $GeO_2$; $HfO_2$; $In_2O$; $In_2O_3$; $I_2O_5$; $PbO$; $MgO$; $SeO_2$; $SiO_2$;

$Ag_2O$; AgO; $Na_2O$; $Na_2O_3$; SrO; $SrO_2$; $ThO_2$; SnO; $SnO_2$; $WO_3$; ZnO; ZrO; $ZrO_2$. In the above group, n in $nH_2O$ is an integer.

Embodiments may use one or more paramagnetic materials chosen from the group: Ce; $Ce_2S_2$; $CsO_2$; $Cr_2(C_2H_3O_2)_3$; $CrCl_2$; $CrCl_3$; $Cr_2(SO_4)_2$; $Cr_2(SO_4)_2 * nH_2O$; $Co(C_2H_3O_2)_2$; $CoBr_2$; $CoCl_2$; $CoCl_2 * nH_2O$; $CoF_2$; $CoI_2$; $Co_3(PO_4)_2$; $CoSO_4$; $Co(SCN)_2$; Dy; $DyO_3$; $Dy_2(SO_4)_3$; $Dy_2(SO_4)_3 * nH_2O$; $Dy_2S_3$; Er; $Er_2O_3$; $Er_2(SO_4)_3 * nH_2O$; $Er_2S_3$; Eu; $EuBr_2$; $EuCl_2$; $EuF_2$; $EuI_2$; $Eu_2O_3$; $EuSO_4$; $Eu_2(SO_4)_3$; $Eu_2(SO_4)_3 * nH_2O$; EuS; Gd; $GdCl_3$; $Gd_2O_3$; $Gd_2(SO_4)_3$; $Gd_2(SO_4)_3 * nH_2O$; $Gd_2S$; $Ho_2O_3$; $Ho_2(SO_4)_3$; $Ho_2(SO_4)_3 * nH_2O$; $FeBr_2$; $FeCO_3$; $FeCl_2$; $FeCl_2 * nH_2O$; $FeCl_3$; $FeCl_3*nH_2O$; $FeF_2$; $FeF_3$; $FeF_3 * nH_2O$; $FeI_2$; $Fe(NO_3)_3 * nH_2O$; FeO; $Fe_2O_3$; $FePO_4$; $FeSO_4$; $FeSO_4*nH_2O$; $Mn(C_2H_3O_2)_2$; $MnBr_2$; $MnCO_3$; $MnCl_2$; $MnCl_2 * nH_2O$; $MnF_2$; $MnF_3$; $Mn(OH)_2$; $MnI_2$; MnO; $Mn_2O_3$; $Mn_3O_4$; $Mn_5O_4$; $MnSO_4 * nH_2O$; MnS; Nd; $NdF_3$; $Nd(NO_3)_3$; $Nd_2O_3$; $Nd_2(SO_4)_3$; $Nd_2S_3$; $NiBr_2$; $NiCl_2$; $NiCl_2 * nH_2O$; $Ni(OH)_2$; Re; $Ta_2O_5$; Tb; $Tb_2O_3$; $Tb(SO_4)_3$; $Tb(SO_4)_3 * nH_2O$; Tm; $Tm_2O_3$; $V_2O_3$; $V_2S_3$; $WS_2$; $Yb_2S_3$; $Y_2O_3$.

For some embodiments, volume magnetic susceptibility may be considered balanced if the susceptibility (when using SI units) is in the range of –50 ppm to 50 ppm (where ppm means parts per million). That is, for some embodiments, diamagnetic or paramagnetic material may be added to biocompatible materials used for implants such that the magnetic susceptibility is in the range of $-50*10^{-6}$ to $50*10^{-6}$ (SI units). This particular range incorporates volume magnetic susceptibilities of air (0.38 ppm), water (–9.0 ppm), and various organic materials (approximately 6 ppm).

Figure 2:
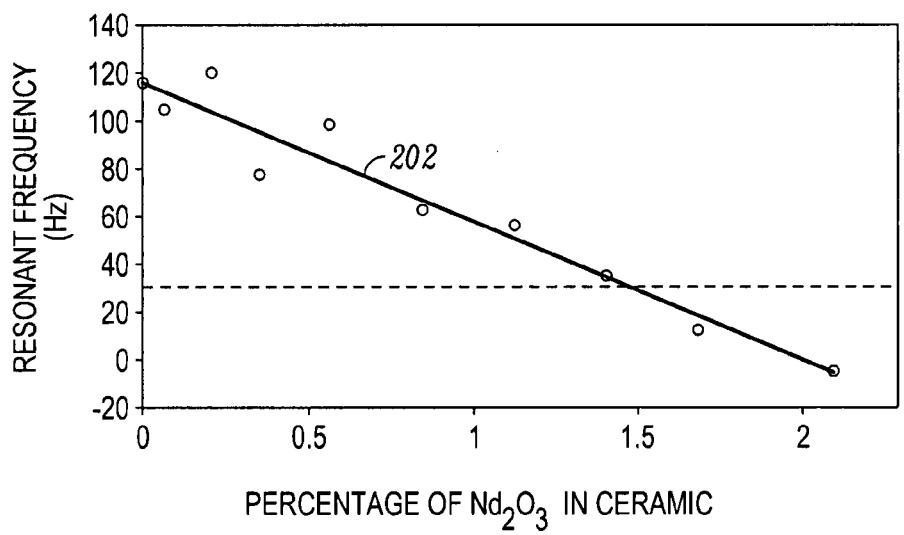
FIG. 2 illustrates measured resonant frequencies at two locations, with one location including an embodiment of the present invention.

Other materials may be used in other embodiments. For example, Table 1 and the accompanying FIG. 2 provide experimental results of adding neodymium oxide, $Nd_2O_3$, a paramagnetic material, to a ceramic. The ceramic used was 750 Rescor™ Cercast ceramic, a product from Cortronics Corp. of Brooklyn, N.Y. The "750 Mix" referred to in the first column of Table 1 is this ceramic product. The "750 Activator" is a product provided by Cortronics Corp. that is used with the 750 Mix to form the ceramic. The third column in Table 1 provides the gram weight of the added $Nd_2O_3$.

The resulting ceramic was placed on a 500 ml square bottle. For each mixture, the NMR resonant frequency was measured at two locations (one near the ceramic sample that was tested and one further away), and the difference in frequency was plotted as a circle in FIG. 2. Line 202 is an interpolated line through these measurements. Dashed line 204 is the measured resonant frequency at a different location in the bottle that does not have the ceramic (air only). The intersection of the interpolated line and dashed line provides the percentage concentration of $Nd_2O_3$ in which the magnetic susceptibility of the ceramic matches that of air. In the particular example of FIG. 2, the concentration of $Nd_2O_3$ at the intersection is approximately 1.5 percent.

TABLE 1

| 750 Mix (g) | 750 Activator (g) | $Nd_2O_3$ (g) |
|---|---|---|
| 7 | 1.8 | 0 |
| 7 | 1.8 | 0.005 |
| 7 | 1.8 | 0.015 |
| 7 | 1.8 | 0.025 |
| 7 | 1.8 | .040 |
| 7 | 1.8 | .060 |
| 7 | 1.8 | .080 |
| 7 | 1.8 | .100 |
| 7 | 1.8 | .120 |
| 7 | 1.8 | .150 |

Figure 3:
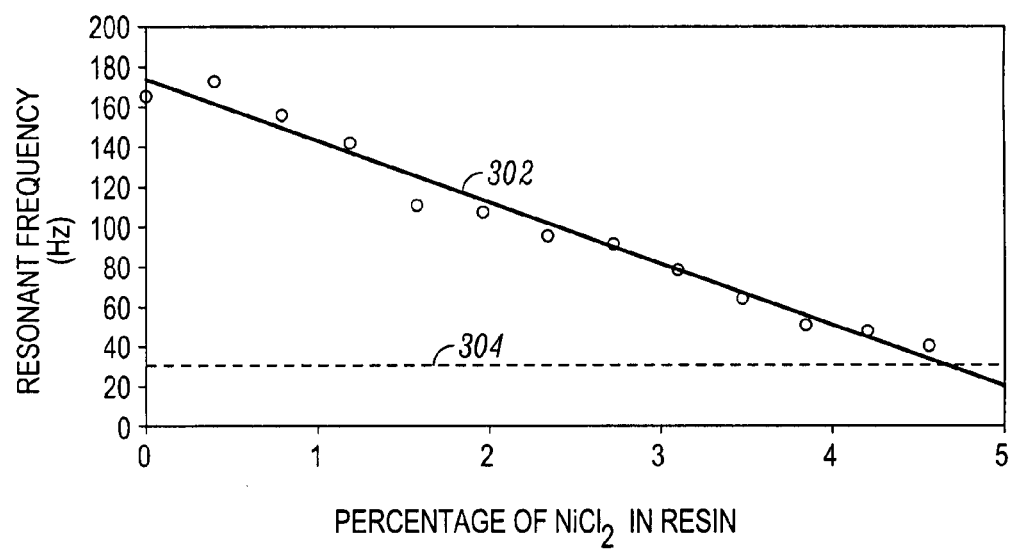
FIG. 3 illustrates measured resonant frequencies at two locations, with one location including another embodiment of the present invention.

As another example, Table 2 and the accompanying FIG. 3 provide experimental results of adding nickel (II) chloride, $NiCl_2*6H_2O$, a paramagnetic, to a polymer. The polymer used was an acrylic resin manufacture by Harry J. Bosworth company, marketed as Duz-All®. This is referred to in the first column of Table 2 as "Acrylic Resin". The second column in Table 2 is the gram weight of an activator used with the acrylic resin. This is referred to as "MMA" for methlymethacrylate monomer. The third column in Table 2 provides the gram weight of the added $NiCl_2*6H_2O$.

The resulting acrylic was placed on a 500 ml square bottle, and for each mixture the NMR resonant frequency was measured at two locations (one near the ceramic sample that was tested and one further away), and the difference in frequency was plotted as a circle in FIG. 3. Line 302 is an interpolated line through these measurements. Dashed line 304 is the measured resonant frequency at a different location in the bottle that does not have the polymer resin (air only). The intersection of the interpolated line and dashed line provides the percentage concentration of $NiCl_2$ in which the magnetic susceptibility of the polymer resin matches that of air. In the particular example of FIG. 3, the concentration of $NiCl_2$ at the intersection is close to 4.7 percent.

TABLE 2

| Acrylic Resin (g) | MMA (g) | $NiCl_2 * 6H_2O$ (g) |
|---|---|---|
| 5 | 2.7 | 0 |
| 5 | 2.7 | 0.02 |
| 5 | 2.7 | 0.04 |
| 5 | 2.7 | 0.06 |
| 5 | 2.7 | 0.08 |
| 5 | 2.7 | 0.10 |
| 5 | 2.7 | 0.12 |
| 5 | 2.7 | 0.14 |
| 5 | 2.7 | 0.16 |
| 5 | 2.7 | 0.18 |
| 5 | 2.7 | 0.20 |
| 5 | 2.7 | 0.22 |
| 5 | 2.7 | 0.24 |

Methods other than that discussed in relation to FIGS. 2 and 3 may be used to determine the concentration of a diamagnetic or paramagnetic additive to ceramic or polymer medical implant material. For example, the susceptibility may be measured directly rather than measuring the resonant frequency at two different locations, one location with the ceramic or polymer, and one location without.

For some embodiments, the susceptibility of the implant material with additive may be adjusted to fall within some specified interval, or within some percent error from a specified target. For example, if the surrounding tissue or environment has a susceptibility $\chi_0$, then additives may be added so that the susceptibility $\chi_m$ of the resulting mixture is such that $\chi_m \in [\chi_0(1-\Delta), \chi_0(1+\Delta)]$. More generally, $\chi_m \in [\chi_L, \chi_U]$, where $\chi_L$ is a lower bound to the interval and $\chi_U$ is an upper bound to the interval.

Although the subject matter has been described in language specific to structural features and methodological acts, it is to be understood that the subject matter defined in the appended claims is not necessarily limited to the specific features or acts described above. Rather, the specific features and acts described above are disclosed as example forms of implementing the claims. Accordingly, various modifications may be made to the described embodiments without departing from the scope of the invention as claimed below.

What is claimed is:

1. An article of manufacture comprising:

a diamagnetic material; and paramagnetic material selected from the group consisting of Ce; $Ce_2S_2$; $CsO_2$; $Cr_2(C_2H_3O_2)_3$; $CrCl_2$; $CrCl_3$; $Cr_2(SO_4)_2$; $Cr_2(SO_4)_2*nH_2O$; $Co(C_2H_3O_2)_2$; $CoBr_2$; $CoCl_2$; $CoCl_2*nH_2O$; $CoF_2$; $CoI_2$; $Co_3(PO_4)_2$; $CoSO_4$; $Co(SCN)_2$; Dy; $DyO_3$; $Dy_2(SO_4)_3$; $Dy_2(SO_4)_3*nH_2O$; $Dy_2S_3$; Er; $Er_2O_3$; $Er_2(SO_4)_3*nH_2O$; $Er_2S_3$; Eu; $EuBr_2$; $EuCl_2$; $EuF_2$; $EuI_2$; $Eu_2O_3$; $EuSO_4$; $Eu_2(SO_4)_3$; $Eu_2(SO_4)_3*nH_2O$; EuS; Gd; $GdCl_3$; $Gd_2O_3$; $Gd_2(SO_4)_3$; $Gd_2(SO_4)_3*nH_2O$; $Gd_2S$; $Ho_2O_3$; $Ho_2(SO_4)_3$; $Ho_2(SO_4)_3*nH_2O$; $FeBr_2$; $FeCO_3$; $FeCl_2$; $FeCl_2*nH_2O$; $FeCl_3$; $FeCl_3*nH_2O$; $FeF_2$; $FeF_3$; $FeF_3*nH_2O$; $FeI_2$; $Fe(NO_3)_3*nH_2O$; FeO; $Fe_2O_3$; $FePO_4$; $FeSO_4$; $FeSO_4*nH_2O$; $Mn(C_2H_3O_2)_2$; $MnBr_2$; $MnCO_3$; $MnCl_2$; $MnCl_2*nH_2O$; $MnF_2$; $MnF_3$; $Mn(OH)_2$; $MnI_2$; MnO; $Mn_2O_3$; $Mn_3O_4$; $Mn_5O_4$; $MnSO_4*nH_2O$; MnS; Nd; $NdF_3$; $Nd(NO_3)_3$; $Nd_2O_3$; $Nd_2(SO_4)_3$; $Nd_2S_3$; $NiBr_2$; $NiCl_2$; $NiCl_2*nH_2O$; $Ni(OH)_2$; Re; $Ta_2O_5$; Tb; $Tb_2O_3$; $Tb(SO_4)_3$; $Tb(SO_4)_3*nH_2O$; Tm; $Tm_2O_3$; $V_2O_3$; $V_2S_3$; $WS_2$; $Yb_2S_3$; and $Y_2O_3$; where n in $nH_2O$ is an integer;

wherein the article of manufacture has a magnetic susceptibility selected from the group consisting of $0.38*10^{-6}$; $-9.0*10^{-6}$; and $6*10^{-6}$.

2. An article of manufacture comprising:

a paramagnetic material; and a diamagnetic material selected from the group consisting of $Al_2O_3$; $Al_2(SO_4)_3$; $Al2(SO_4)_3*2H_2O$; $Sb_2O_3$; BaO; $BaO_2$; Bi; $BiI_3$; BiO; $Bi_2(SO_4)_3$; $Bi_2S_3$; $B_2O_3$; $Ca(C_2H_3O_2)_2$; $CaBr_2*nH_2O$; $GaI_3$; $Ga_2O$; GeO; $GeO_2$; $HfO_2$; $In_2O$; $In_2O_3$; $In_2O_5$; PbO; MgO; $SeO_2$; $SiO_2$; $Ag_2O$; AgO; $Na_2O$; $Na_2O_3$; SrO; $SrO_2$; $ThO_2$; SnO; $SnO_2$; $WO_3$; ZnO; ZrO; and $ZrO_2$; where n in $nH_2O$ is an integer;

wherein the article of manufacture has a magnetic susceptibility selected from the group consisting of $0.38*10^{-6}$; $-9.0*10^{-6}$; and $6*10^{-6}$.

* * * * *